(12) United States Patent
Stierstorfer

(10) Patent No.: US 6,574,296 B2
(45) Date of Patent: Jun. 3, 2003

(54) COMPUTER TOMOGRAPHY UNIT AND METHOD FOR OPERATING SAME

(75) Inventor: Karl Stierstorfer, Erlangen (DE)

(73) Assignee: Siemens Aktiengesellschaft, Münich (DE)

( * ) Notice: Subject to any disclaimer, the term of this patent is extended or adjusted under 35 U.S.C. 154(b) by 0 days.

(21) Appl. No.: 09/955,446

(22) Filed: Sep. 18, 2001

(65) Prior Publication Data
US 2002/0067793 A1 Jun. 6, 2002

(30) Foreign Application Priority Data
Sep. 18, 2000 (DE) .......................... 100 46 091

(51) Int. Cl.[7] .............................................. A61B 6/03
(52) U.S. Cl. .................... 378/15; 378/4; 378/16
(58) Field of Search ............................ 378/4, 62, 63, 378/98.8, 205, 206, 20, 15, 16

(56) References Cited

U.S. PATENT DOCUMENTS 5,954,647 A * 9/1999 Bova et al. .................. 378/205
6,041,249 A    3/2000 Regn
6,050,724 A * 4/2000 Schmitz et al. ............. 378/205
6,088,424 A * 7/2000 Postlethwaite ............... 378/63
6,227,704 B1 * 5/2001 Bani-Hashemi et al. ...... 378/63
6,229,873 B1 * 5/2001 Bani-Hashemi et al. ...... 378/63
6,272,204 B1 * 8/2001 Amtower et al. ............. 378/63
6,435,717 B1 * 8/2002 Kohler et al. ................. 378/63

* cited by examiner

Primary Examiner—Drew A. Dunn
(74) Attorney, Agent, or Firm—Schiff Hardin & Waite

(57) ABSTRACT

In a computed tomography and a method for operating a computed tomography unit, in order to scan an object under investigation a radiation source emits a pyramid-shaped X-ray beam, which penetrates through the object under examination and strikes a radiation detector. The computer tomography unit has an optical recording device which, during the scanning, records optical images of a partial surface of the object, which faces the X-ray source and through which the pyramid-shaped X-ray beam has penetrated. An image of the surface of the object under examination is constructed from optical images obtained in this manner this image is assigned to a sectional image obtained by means of the scan, or to an overview image.

7 Claims, 1 Drawing Sheet

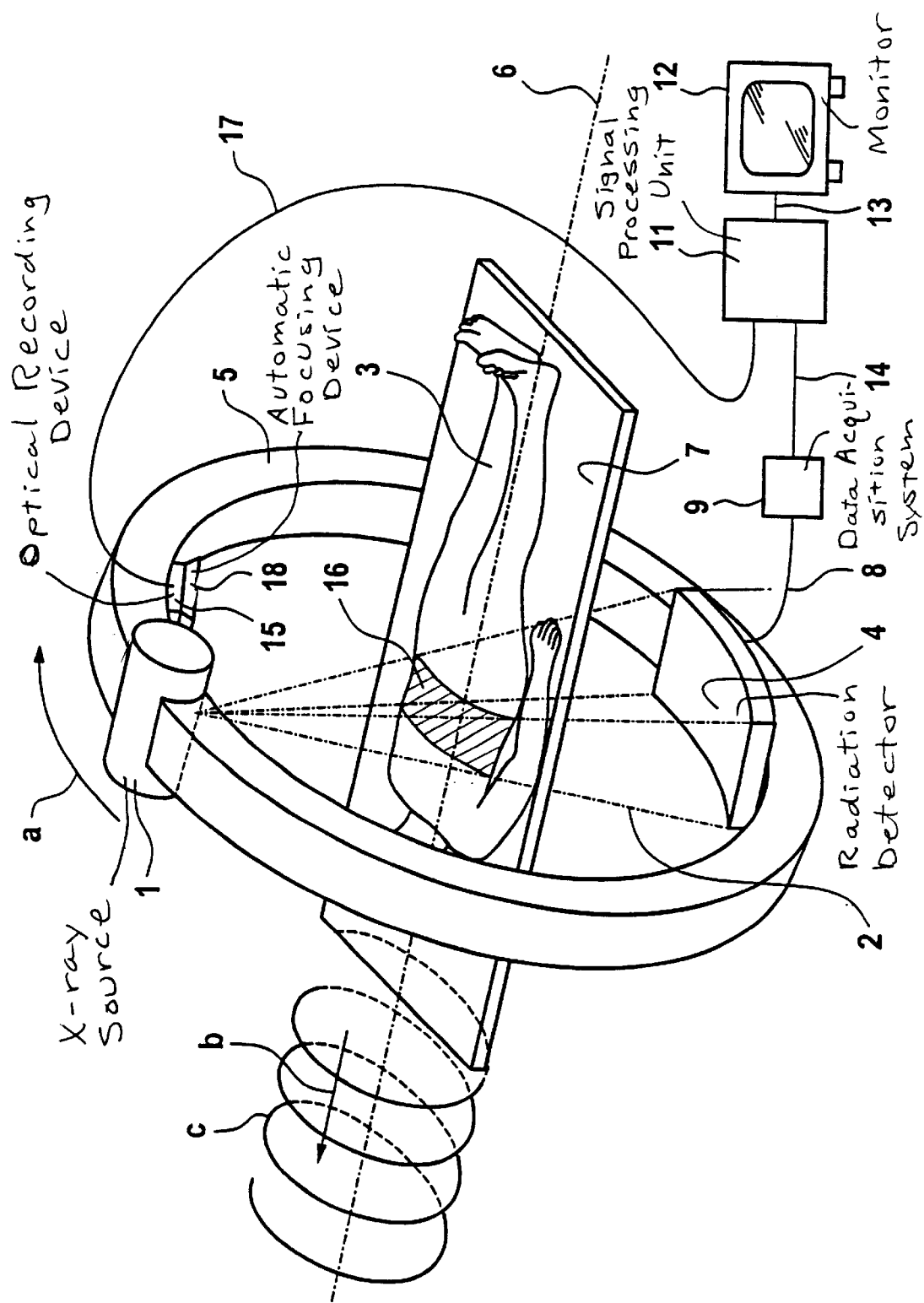

COMPUTER TOMOGRAPHY UNIT AND METHOD FOR OPERATING SAME

BACKGROUND OF THE INVENTION

1. Field of the Invention

The present invention relates to a computed tomography unit, having a radiation detector and an X-ray source. The invention also relates to a method for operating a computed tomography unit of this type.

2. Description of the Prior Art

A computed tomography unit of the type described above has an X-ray source which directs a pyramid-shaped X-ray beam through an object under examination, for example a patient, onto a radiation detector. The X-ray source and, depending on the design of the computed tomography unit, also the radiation detector are arranged, on a gantry which is able to rotate around the patient. The patient can lie on a table which can be shifted or moved along a system axis relative to the gantry. In this way it is possible, inter alia, to helically scan a region of the patient's body, so that a volume of the patient's body being scanned during the scan. Sectional images of planar layers or slices of the patient's body are reconstructed from the measured values obtained. If the gantry does not rotate during a scan, but rather the table is simply moved along the system axis, it is possible to compile an overview image (topogram) of the patient.

To assign a region of the patient's body to sectional images or to an overview image obtained by means of the scan, a treating physician can orient himself or herself from, for example, features known as anatomical land marks, which can be seen both in the sectional image or the overview pictures and on the patient. Orientation by means of a laser sight which may be present in front of the gantry also is possible. A laser sight of this type is described, for example, in U.S. Pat. No. 6,041,249.

A drawback of these methods, however, is the inaccuracy and difficulty in assigning a particular sectional image to the corresponding region of the patient's body.

SUMMARY OF THE INVENTION

An object of the present invention is to provide a computed tomography unit of the type initially described with which it is easier to assign a sectional image or an overview picture to a corresponding region of a patient's body. A further object of the invention is to provide a method for operating a computed tomography unit of this type which facilitates this object.

According to the invention, the first object is achieved in a computed tomography unit, having a radiation detector and a X-ray source, which in order to scan an object under examination emits a pyramid-shaped X-ray beam, which penetrates through the object under examination, and wherein the computed tomography unit has an optical recording device which, during the scanning, records optical images of a partial surface, which faces the X-ray source and through which the pyramid-shaped X-ray beam has penetrated, of the object under examination. In this way, for example after a patient has been scanned, the optical images can be compared with tomographs or overview images obtained by means of the scan, and this can advantageously be utilized to assign in particular sectional images to the regions of the patient's body.

In an embodiment of the invention, the optical recording device is arranged on a rotating part of the gantry of the computed tomography unit, and given a suitable arrangement of the optical recording device on the gantry, conditions are established which enable the optical recording device always to be oriented in a defined position relative to the X-ray source and in particular onto the partial surface of the patient through which the X-ray beam penetrates during the recording of a computed tomograph.

In an embodiment of the invention, the optical recording device has at least one charge-coupled device (CCD) linear array.

In a variant of this embodiment, the optical recording device has an automatic focusing device, allowing sharply defined optical images to be obtained.

In a further embodiment, the optical images are processed further by a signal-processing unit. Therefore, it is possible to electronically assign the sectional images or overview pictures obtained by means of the scan to the regions of the object under examination.

The other object of the invention is achieved in a method for operating a computed tomography unit, having a radiation detector and an X-ray source, which in order to scan an object under investigation emits a pyramid-shaped X-ray beam, which penetrates through the object under examination, the computed tomography unit having an optical recording device which, during the scanning, records optical images of a partial surface, which faces the X-ray source and through which the pyramid-shaped X-ray beam has penetrated, of the object under examination, having the following method steps:

a) recording an optical image at each scanning step, b) constructing an image of a surface of the object under examination from optical images of the partial surfaces which have been penetrated by the pyramid-shaped X-ray beam during the scanning, and c) assigning the image to a sectional image obtained by means of the scan or an overview picture (topogram).

This allows the image of the surface to be compared with the sectional images or overview images after a scan and, in particular, allow regions of an examined patient's body to be assigned to sectional images.

In another embodiment of the invention, a signal-processing unit constructs the image of the surface of the object under examination. Consequently, it is possible to electronically assign the sectional images or the overview picture to the regions of the object under examination.

DESCRIPTION OF THE DRAWING

The single FIGURE is a schematic diagram of a computed tomography unit constructed and operating in accordance with the principles of the present invention.

DESCRIPTION OF THE PREFERRED EMBODIMENTS

The FIGURE schematically depicts a computed tomography unit according to the invention, having an X-ray source 1, which emits a pyramid-shaped X-ray beam 2, the edge rays of which are illustrated by dot-dashed lines in the FIGURE. The beam 2 passes through an object under examination, for example a patient 3, and strikes a radiation detector 4. In the exemplary embodiment, the X-ray source 1 and the radiation detector 4 are arranged opposite one another on an annular gantry 5. The gantry 5 is mounted on a holding device (not shown in the FIGURE) in such a manner that it can rotate (cf. arrow a) with respect to a system axis 6 which proceeds through the center of the annular gantry 5.

In the exemplary embodiment, the patient 3 lies on a table 7 which is transparent to X-rays and is mounted so that it can be displaced along the system axis 6 (cf. arrow b) by means of a support fixture, which is not shown in the FIGURE.

The X-ray source 1 and the radiation detector 4 therefore form a measuring system which can rotate with respect to the system axis 6 and can be displaced along the system axis 6 relative to the patient 3, so that radiation can pass through the patient 3 at various projection angles and various positions with respect to the system axis 6. A data-acquisition system 9 uses the output signals which are produced by the radiation detector 4 to form measured values, which are forwarded to a signal-processing unit 11 which calculates an image of the patient 3, which in turn can be displayed on a monitor 12. In the exemplary embodiment, the data-acquisition system 9 is connected to the radiation detector 4 by means of an electrical line 8, which, in a manner which is not illustrated, includes, for example, a slip ring system or a wireless transmission section, the monitor 12 is connected to the signal-processing unit 11 by means of an electrical line 13, and the signal-processing unit 11 is connected to the data-acquisition unit 9 by means of an electrical line 14.

The computed tomography unit shown in the FIGURE can be used for both sequential scanning and spiral scanning.

In the case of sequential scanning, the patient 3 is scanned in slices. In this case, the X-ray source 1 and the radiation detector 4 are rotated around the patient 3 with respect to the system axis 6, and the measurement system comprising the X-ray source 1 and the radiation detector 4 records a multiplicity of projections, in order to scan a two-dimensional slice of the patient 3. A sectional image which represents the scanned slice is reconstructed from the measured values obtained. The patient 3 is in each case moved along the system axis 6 between the scanning of successive slices. This operation is repeated until all the slices of interest have been captured.

During the spiral scan, the measurement system which comprises the X-ray source 1 and the radiation detector 4 rotates with respect to the system axis 6, and the table 7 moves continuously in the direction of the arrow b, i.e. the measurement system comprising the X-ray source 1 and the radiation detector 4 moves continuously along a helical path c relative to the patient 3 until the area of the patient 3 which is of interest has been completely captured. In the process, a volume data set is generated. From this, the signal-processing unit 11 uses an interpolation method to calculate planar data, from which, as with sequential scanning, sectional images are reconstructed.

Furthermore, the computed tomography unit illustrated in the FIGURE can also be used to produce an overview image (topogram or X-ray shadow image).

For an overview image, the measurement system comprising the X-ray source 1 and the radiation detector 4 is moved into an angular position which is desired for the overview picture. Then, the table 7 moves relative to the measurement system comprising the X-ray source 1 and the radiation detector 4, as indicated by arrow b, until the area of the patient for which the overview picture is to be generated has been completely captured.

On the gantry 5 there is an optical recording device 15 which, in the exemplary embodiment, is formed by at least one charge-coupled device (CCD) linear array. Other optical recording devices 15 are also possible.

The optical recording device 15 is arranged on the gantry 5 so that, while the patient 3 is being scanned, in particular for an overview image, a sequential scan or a spiral scan, it is able to record optical images of partial surfaces 16 of the patient 3 which face the X-ray source 1 and through which the X-ray beam 2 has penetrated. To obtain sharply defined optical images, the optical recording device 15 has an automatic focusing device 18, in order to be able to cope with different sizes of patient 3. The optical recording device 15 also may have a fixed focusing system with a sufficient depth of field. The thickness of the partial surface 16 in the direction of the system axis 6 in this case corresponds to the layer thickness of a layer recorded using the computer tomography unit shown in the FIGURE. It is also possible to generate optical images of other partial surfaces which include the partial surface 16.

The optical recording device 15 is connected, by means of an electric line 17 which, in a manner which is not illustrated, includes, for example, a slip ring system or a wireless transmission section, to the signal-processing unit 11, which further processes electrical signals from the optical recording device 15, which are assigned to the optical images, and displays them, for example on the monitor 12.

The optical images produced using the optical recording device 15 can be used in particular to assign the sectional images or an overview image to the corresponding body regions of the patient 3 using the following method:

During the scan, an optical image is recorded for each step of the scan. Consequently, a sufficiently large number of optical images to cover the entire surface of the patient 3 through which the X-ray beam 2 has penetrated during the scan are compiled.

In a first operating mode, the signal-processing unit 11 then produces in particular an image from the individual optical images which represents the entire surface or partial surface of the surface area through which the X-ray beam 2 has penetrated during the scan.

In a second operating mode, the signal-processing unit 11 constructs images of a surface of the patient 3 which show the patient 3 or parts of the patient 3 from different perspectives.

Moreover, the computed tomography unit can be operated so that the image of the surface is displayed on the monitor 12 together with a desired sectional image, the signal-processing unit 11 controlling the monitor 12 for this purpose so that the body region for which the sectional image has been produced is marked on the image of the surface. Therefore, the sectional image is assigned to the corresponding body region of the patient 3 in an advantageous way.

In a further operating mode, an overview picture is superimposed on the image of the surface, or the overview image is displayed next to the image of the surface. This allows easy assignment of the overview picture to body regions of the patient 3.

The optical recording device 15 does not necessarily have to be arranged on the gantry 5. However, this arrangement has the advantage that the X-ray source 1 and the optical recording device 15 are oriented in defined ways relative to one another and therefore the optical recording device 15, during a scan, can easily be directly at the partial surfaces 16 through which the X-ray beam 2 penetrates during a scan.

The computed tomography unit also may have, in a manner which is not illustrated, a lighting system which illuminates in particular the partial surfaces 16 during a scan, in order to produce better optical images.

The images of the surface may also be assigned to 3D-reconstructions, so-called maximum intensity projections or multiplanar reconstructions of the 3D-data set.

The object under examination does not necessarily have to be human, as suggested by the FIGURE.

Although modifications and changes may be suggested by those skilled in the art, it is the intention of the inventor to embody within the patent warranted hereon all changes and modifications as reasonably and properly come within the scope of his contribution to the art.

I claim as my invention:

1. A computed tomography unit comprising:

a radiation source which emits a pyramid-shaped X-ray beam from a focus adapted to penetrate an examination subject;

an arrangement for rotating said focus continuously around said examination subject;

a radiation detector on which said X-ray beam is incident after passing through said examination subject, said X-ray source and said radiation detector thereby scanning said examination subject with a portion of a surface of said examination subject, facing said X-ray source, having said pyramid-shaped X-ray beam penetrate therethrough; and an optical recording device which, during said scanning, records an optical image of said portion of said surface.

2. A computed tomography unit as claimed in claim 1 said arrangement for rotating said focus is a rotating gantry and wherein said X-ray source and said radiation detector are disposed on said rotating gantry, and wherein said optical recording device is also disposed on said gantry.

3. A computed tomography unit as claimed in claim 1 wherein said optical recording device comprises at least one charge coupled device linear array.

4. A computed tomography unit as claimed in claim 1 wherein said optical recording device has an automatic focusing device.

5. A computed tomography unit as claimed in claim 1 further comprising a signal processing unit for processing said optical images.

6. A method for operating a computed tomography unit, comprising the steps of:

scanning an examination subject by emitting a pyramid-shaped X-ray beam from a focus, which penetrates the examination subject, while rotating said focus continuously around the examination subject, and detecting X-rays from said X-ray beam after penetrating said subject with a radiation detector, said scan producing a scan image selected from the group consisting of a diagnostic image and an overview image, said scanning proceeding in a plurality of scanning steps;

recording an optical image of a portion of a surface of said examination subject penetrated by said X-ray beam for each scanning step;

constructing an image of a surface of said subject from a plurality of said optical images; and assigning said image of said surface to a slice image obtained from said scanning.

7. A method as claimed in claim 6 comprising constructing said image of said surface of said subject in a signal processing unit.

* * * * *